(12) United States Patent
Ou Yang et al.

(10) Patent No.: US 11,638,530 B2
(45) Date of Patent: May 2, 2023

(54) BLOOD PRESSURE MEASUREMENT DEVICE AND CALCULATION METHOD THEREOF

(71) Applicant: AViTA Corporation, New Taipei (TW)

(72) Inventors: Hsing Ou Yang, New Taipei (TW); Jui-Yang Huang, New Taipei (TW); I-Chih Huang, New Taipei (TW)

(73) Assignee: AVITA CORPORATION, New Taipei (TW)

( * ) Notice: Subject to any disclaimer, the term of this patent is extended or adjusted under 35 U.S.C. 154(b) by 423 days.

(21) Appl. No.: 16/882,538

(22) Filed: May 24, 2020

(65) Prior Publication Data

US 2020/0367768 A1 Nov. 26, 2020

(30) Foreign Application Priority Data

May 24, 2019 (TW) .................................. 108118124

(51) Int. Cl.
*A61B 5/021* (2006.01)
*A61B 5/022* (2006.01)
(Continued)

(52) U.S. Cl.
CPC ........ *A61B 5/02141* (2013.01); *A61B 5/0225* (2013.01); *A61B 5/0235* (2013.01);
(Continued)

(58) Field of Classification Search
None
See application file for complete search history.

(56) References Cited

U.S. PATENT DOCUMENTS 9,532,722 B2 1/2017 Lamego et al.
2009/0012412 A1* 1/2009 Wiesel .................. A61B 5/024
600/508
(Continued)

FOREIGN PATENT DOCUMENTS

TW 201228634 7/2012
TW M460634 9/2013
(Continued)

*Primary Examiner* — Matthew Kremer
*Assistant Examiner* — Matthew Eric Ogles
(74) *Attorney, Agent, or Firm* — Raymond Chan

(57) ABSTRACT

A blood pressure measurement device and a calculation method thereof are disclosed. The blood pressure measurement device includes a pressurizing motor unit and an exhaust valve unit in communication with an airbag unit. The blood pressure calculation method includes steps of controlling the pressurizing motor unit to pressurize the airbag unit; measuring pressurized measurement data from the airbag unit in a pressurization process; controlling the pressurizing motor unit to stop pressurizing the airbag unit, and controlling the exhaust valve unit to depressurize the airbag unit; measuring depressurized measurement data from the airbag unit in a depressurization process; extracting blood pressure parameters from the pressurized measurement data and the depressurized measurement data; calculating an average of the blood pressure parameters extracted from the pressurized measurement data and the depressurized measurement data, to obtain a blood pressure measurement result.

4 Claims, 5 Drawing Sheets

(51) Int. Cl.
*A61B 5/0225* (2006.01)
*A61B 5/0235* (2006.01)
*A61B 5/00* (2006.01)

(52) U.S. Cl.
CPC ...... *A61B 5/02116* (2013.01); *A61B 5/02233* (2013.01); *A61B 5/742* (2013.01)

(56) References Cited

U.S. PATENT DOCUMENTS

| | | | |
|---|---|---|---|
| 2012/0330112 A1* | 12/2012 | Lamego | A61B 5/02233 600/483 |
| 2015/0045679 A1* | 2/2015 | St. Pierre | A61B 5/0225 600/483 |
| 2016/0228017 A1* | 8/2016 | Frick | A61B 5/7278 |
| 2018/0160926 A1* | 6/2018 | Chang | A61B 5/361 |
| 2022/0151503 A1* | 5/2022 | Ezoe | A61B 5/02225 |

FOREIGN PATENT DOCUMENTS

| | | | |
|---|---|---|---|
| TW | 201632139 | 9/2016 | |
| WO | WO-2018167361 A1 * | 9/2018 | A61B 5/02125 |

* cited by examiner

BLOOD PRESSURE MEASUREMENT DEVICE AND CALCULATION METHOD THEREOF

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to a measurement device and a measurement method, and more particularly to a blood pressure measurement device and a blood pressure calculation method.

Description of Related Arts

Most of the commercially-available electronic blood pressure measurement devices use the oscillography to measure blood pressures and, for example, use measure data obtained by the single pressurization oscillography or depressurization oscillography to calculate the blood pressure value; however, insufficient samples obtained during the measurement process may cause inaccurate measurement according to oscillography. Conventionally, the oscillography can be implemented by pressurization measurement manner or depressurization measurement manner. The pressurization measurement oscillography is to obtain pulse characteristic signals for further blood pressure analysis during an inflating process, as shown in FIG. 1.

According to the single pressurization oscillography, during the process of slowly inflating an air bag by a pump, the pulse characteristic signals (such as amplitude) are captured to obtain the highest value point, which is defined as an average pressure (Am), and the average pressure (Am) of the pulse characteristic signals is then multiplied by clinical statistical parameters which include a threshold parameter Tsys of systolic blood pressure and a threshold parameter Tdia of diastolic blood pressure, to calculate a systolic pressure pulse characteristic signal (Asys) and a diastolic pressure pulse characteristic signal (Adia), respectively, and then the systolic blood pressure (Psys) and diastolic blood pressure (Pdia) can be found based on the two pulse characteristic signals Asys and Adia, wherein Pm is an average of the systolic blood pressure (Psys) and diastolic blood pressure (Pdia). The calculation formulas are expressed as follows:

$$P_{dia} = \frac{P_m \times A_{dia}}{A_m}, \text{ wherein} \quad (1)$$
$$A_{dia} = T_{dia} \times A_m \rightarrow P_{dia} = P_m \times T_{dia}$$

$$P_{sys} = \frac{P_m \times A_{sys}}{A_m}, \text{ wherein} \quad (2)$$
$$A_{sys} = T_{sys} \times A_m \rightarrow P_{sys} = P_m \times T_{sys}$$

The operation of depressurization measurement oscillography is just the opposite of that of the pressurization measurement oscillography. During operation of the depressurization measurement oscillography, quick pressurization is first performed, and the pulse characteristic signals are then measured for further blood pressure analysis during a slow depressurization process, as shown in FIG. 2. According to the single depressurization oscillography, the air bag is quickly inflated by the pump, and then the pulse characteristic signals (such as amplitude) are captured to obtain the highest value point, which is defined as an average pressure (Am), during the slow depressurization process, and the average pressure (Am) of the pulse characteristic signal is multiplied by clinical statistical parameters which include the threshold parameter Tsys of systolic pressure and the threshold parameter Tdia of diastolic pressure, to calculate the systolic pressure pulse characteristic signal (Asys) and diastolic pressure pulse characteristic signal (Adia), respectively, and then the systolic pressure (Psys) and diastolic pressure (Pdia) can be found based on the two pulse characteristic signals Asys and Adia. The calculation formulas of single depressurization oscillography are the same as the above formulas (1) and (2).

However, during the single pressurization oscillography measurement shown in FIG. 1, the measurement for pulse characteristic is stopped when it is determined the systolic pressure (Psys) is captured, and this scheme may terminate measurements for some subjects because of misjudgment for the systolic pressure even if the correct systolic blood pressure is not captured; in the other hand, during the single depressurization oscillography measurement shown in FIG. 2, the measurement of the pulse characteristic is stopped when it is determined that the diastolic pressure (Pdia) is captured, but this scheme may terminate the measurement for some subjects because of misjudgment of the diastolic pressure even if the correct diastolic pressure is not captured.

Furthermore, the analysis of atrial fibrillation in the prior art uses the electrocardiogram measurement method, and then uses the heartbeat interval to determine atrial fibrillation. Therefore, conventional electronic blood pressure measurement device cannot determine atrial fibrillation by electrocardiographic measurement.

Therefore, the present invention is to develop a blood pressure measurement device and a blood pressure calculation method thereof to preclude the measurement inaccuracy caused by the misjudgment of the blood pressure measurement device, and adopt correct measurement data to improve accuracy of the obtained systolic pressure (Psys) and diastolic pressure (Pdia), so as to improve industrially applicability of the blood pressure measurement device.

SUMMARY OF THE PRESENT INVENTION

An objective of the present invention is to prevent a condition that the blood pressure measurement device determines wrong measurement data for extracting pulse characteristic signals, so as to extract correct measurement data to improve the accuracy of measuring a systolic pressure (Psys) and a diastolic pressure (Pdia), thereby providing a blood pressure measurement device and a blood pressure calculation method.

In order to achieve the objective, the present invention provides a blood pressure calculation method applied to a blood pressure measurement device including a pressurizing motor unit and at least one exhaust valve unit in communication with an airbag unit, and the blood pressure calculation method includes steps of controlling the pressurizing motor unit to pressurize the airbag unit; measuring pressurized measurement data from the airbag unit during a pressurization process; controlling the pressurizing motor unit to stop pressurizing the airbag unit, and then controlling the at least one exhaust valve unit to depressurize the airbag unit; measuring depressurized measurement data from the airbag unit during a depressurization process; extracting at least one blood pressure parameter from each of the pressurized measurement data and the depressurized measurement data; and calculating an average of the blood pressure parameters extracted from the pressurized measurement data and the depressurized measurement data, to obtain a blood pressure measurement result.

According to an embodiment, the blood pressure calculation method of the present invention further includes steps of extracting maximum amplitude data in pressurized measurement and maximum amplitude data in depressurized measurement from the pressurized measurement data and the depressurized measurement data, respectively; calculating an average of the maximum amplitude data in pressurized measurement and the maximum amplitude data in depressurized measurement; calculating a product of the average and a threshold parameter of the systolic pressure in depressurized measurement, and using the calculated product as an amplitude threshold of the systolic pressure in depressurized measurement; extracting or deducing pressure data from the depressurized measurement data based on the amplitude threshold of the systolic pressure in depressurized measurement, and using the pressure data as a systolic pressure value of the blood pressure measurement result.

According to an embodiment, the blood pressure calculation method of the present invention further includes steps of extracting maximum amplitude data in pressurized measurement and maximum amplitude data in depressurized measurement; calculating an average of the maximum amplitude data in pressurized measurement and the maximum amplitude data in depressurized measurement; calculating a product of the average and a threshold parameter of the diastolic pressure in pressurized measurement, and using the calculated product as an amplitude threshold of the diastolic pressure in pressurized measurement; extracting or deducing pressure data from the pressurized measurement data based on the amplitude threshold of the diastolic pressure in pressurized measurement, and using the pressure data as a diastolic pressure value of the blood pressure measurement result.

In order to achieve the objective, the present invention further provides a blood pressure measurement device including an airbag unit, a pressurizing motor unit, at least one exhaust valve unit, a sensing unit, a display unit, a memory and a processing unit. The pressurizing motor unit is in communication with the airbag unit. The at least one exhaust valve unit is in communication with the airbag unit. The sensing unit is configured to obtain measurement data from the airbag unit. The display unit is configured to display a blood pressure measurement result. The memory is configured to store a program instruction set. The processing unit is configured to execute the program instruction set to control the pressurizing motor unit to pressurize the airbag unit; receive pressurized measurement data from the sensing unit during a pressurization process; control the pressurizing motor unit to stop pressurizing the airbag unit, and then control the exhaust valve unit to depressurize the airbag unit; receive depressurized measurement data from the sensing unit during a depressurization process; extracting at least one blood pressure parameter from each of the pressurized measurement data and the depressurized measurement data; calculate an average of the blood pressure parameters extracted from the pressurized measurement data and the depressurized measurement data, to obtain a blood pressure measurement result.

According to an embodiment, the processing unit of the blood pressure measurement device is configured to execute the program instruction set to: extract maximum amplitude data in pressurized measurement and maximum amplitude data in depressurized measurement from the pressurized measurement data and the depressurized measurement data, respectively; calculate an average of the maximum amplitude data in pressurized measurement and the maximum amplitude data in depressurized measurement; calculate a product of the average and a threshold parameter of the systolic pressure in depressurized measurement, and use the calculated product as an amplitude threshold of the systolic pressure in depressurized measurement; extract or deduce pressure data from the depressurized measurement data based on the amplitude threshold of the systolic pressure in depressurized measurement, and use the pressure data as a systolic pressure value of the blood pressure measurement result.

According to an embodiment, the processing unit of the blood pressure measurement device further executes the program instruction set to: extract maximum amplitude data in pressurized measurement and maximum amplitude data in depressurized measurement from the pressurized measurement data and the depressurized measurement data, respectively; calculate an average of the maximum amplitude data in pressurized measurement and the maximum amplitude data in depressurized measurement; calculate a product of the average and a threshold parameter of the diastolic pressure in pressurized measurement, and use the calculated product as an amplitude threshold of the diastolic pressure in pressurized measurement; extract or deduce pressure data from the pressurized measurement data based on the amplitude threshold of the diastolic pressure in pressurized measurement, and use the pressure data as a diastolic pressure value of the blood pressure measurement result.

According to the blood pressure measurement device and the blood pressure calculation method of the present invention, during the single cycle of pressurization and depressurization, the pressurized measurement data and depressurized measurement data are extracted, respectively, and the correct measurement data can be extracted from the pressurized measurement data and depressurized measurement data, so that the accuracy of obtaining systolic pressure (Psys) and the diastolic pressure (Pdia) can be improved.

BRIEF DESCRIPTION OF THE DRAWINGS

The structure, operating principle and effects of the present invention will be described in detail by way of various embodiments which are illustrated in the accompanying drawings.

DETAILED DESCRIPTION OF THE PREFERRED EMBODIMENT

Figure 1:
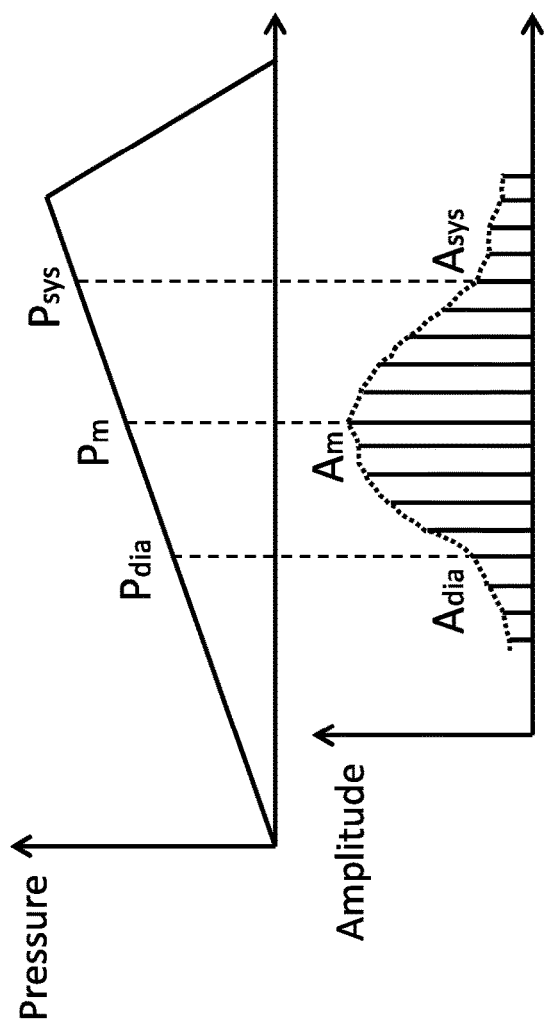
FIG. 1 is a schematic view of a pulse signal and pressure values measured by the conventional single-pressurization oscillography.

The following embodiments of the present invention are herein described in detail with reference to the accompanying drawings. These drawings show specific examples of the embodiments of the present invention. These embodiments are provided so that this disclosure will be thorough and complete, and will fully convey the scope of the invention to those skilled in the art. It is to be acknowledged that these embodiments are exemplary implementations and are not to be construed as limiting the scope of the present invention in any way. Further modifications to the disclosed embodiments, as well as other embodiments, are also included within the scope of the appended claims. These embodiments are provided so that this disclosure is thorough and complete, and fully conveys the inventive concept to those skilled in the art. Regarding the drawings, the relative proportions and ratios of elements in the drawings may be exaggerated or diminished in size for the sake of clarity and convenience. Such arbitrary proportions are only illustrative and not limiting in any way. The same reference numbers are used in the drawings and description to refer to the same or like parts.

It is to be acknowledged that, although the terms 'first', 'second', 'third', and so on, may be used herein to describe various elements, these elements should not be limited by these terms. These terms are used only for the purpose of distinguishing one component from another component. Thus, a first element discussed herein could be termed a second element without altering the description of the present disclosure. As used herein, the term "or" includes any and all combinations of one or more of the associated listed items.

It will be acknowledged that when an element or layer is referred to as being "on," "connected to" or "coupled to" another element or layer, it can be directly on, connected or coupled to the other element or layer, or intervening elements or layers may be present. In contrast, when an element is referred to as being "directly on," "directly connected to" or "directly coupled to" another element or layer, there are no intervening elements or layers present.

In addition, unless explicitly described to the contrary, the word "comprise" and variations such as "comprises" or "comprising", will be acknowledged to imply the inclusion of stated elements but not the exclusion of any other elements.

Figure 3:
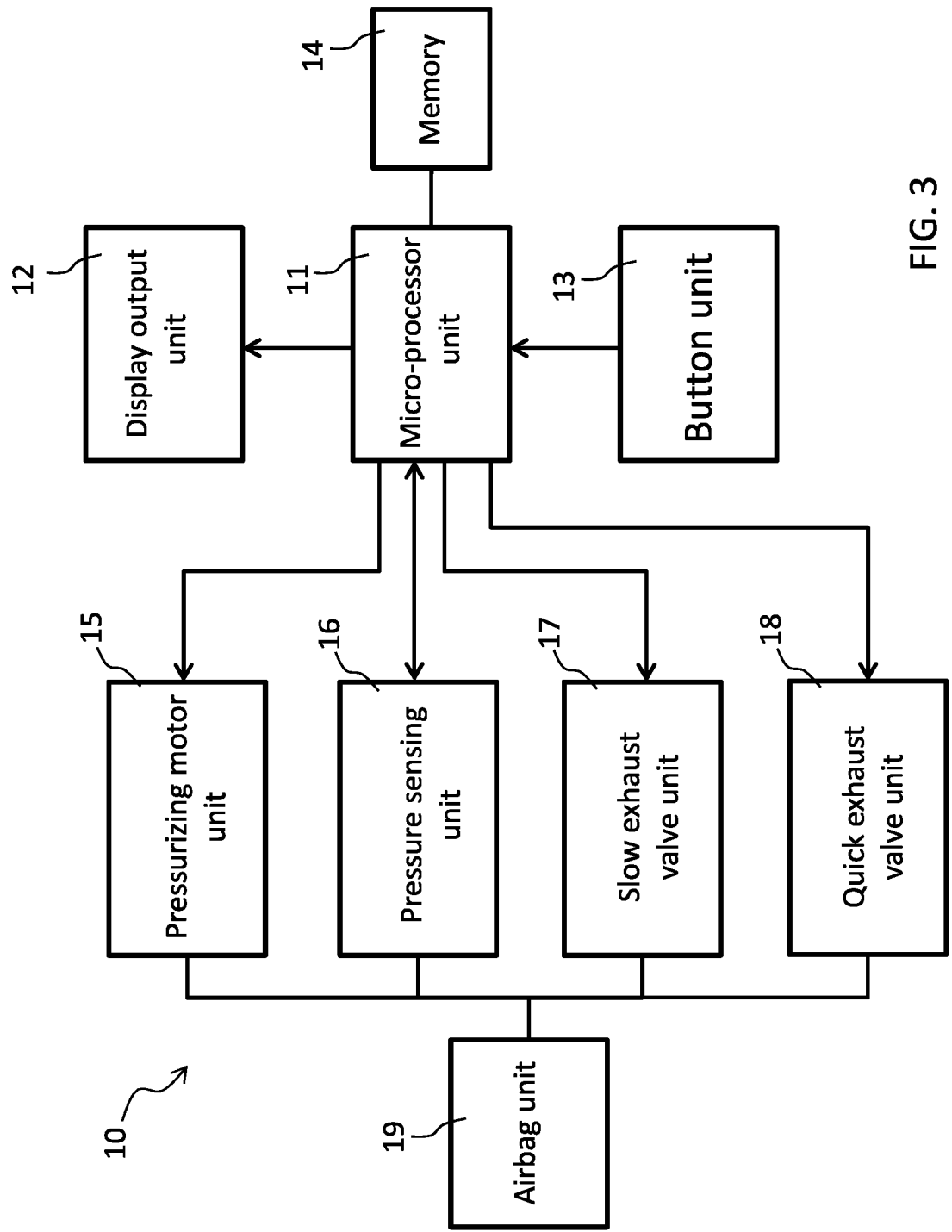
FIG. 3 is a functional block diagram of a blood pressure measurement device of the present invention.

Please refer to FIG. 3, which shows a functional block diagram of a blood pressure measurement device of the present invention. In an embodiment of the present invention, a blood pressure measurement device 10 includes a micro-processor unit 11, a display output unit 12, a button unit 13, a memory 14, a pressurizing motor unit 15, a pressure sensing unit 16, a slow exhaust valve unit 17, a quick exhaust valve unit 18, an airbag unit 19 and a power supply unit. The power supply unit is not shown in FIG. 3 and configured to provide electrical power for the units of the blood pressure measurement device 10. In an embodiment, the airbag unit 19 can be a cuff airbag unit, and the display output unit 12 can be a liquid crystal display (LCD) device. The pressurizing motor unit 15, the slow exhaust valve unit 17, and the quick exhaust valve unit 18 are in communication with the airbag unit 19. The micro-processor unit 11 can control the pressurizing motor unit 15, the slow exhaust valve unit 17 and the quick exhaust valve unit 18, to perform pressurization and depressurization of the airbag unit 19, and the pressure sensing unit 16 can sense the airbag unit 19 and the micro-processor unit 11 obtains measurement data from the pressure sensing unit 16.

Figure 4:
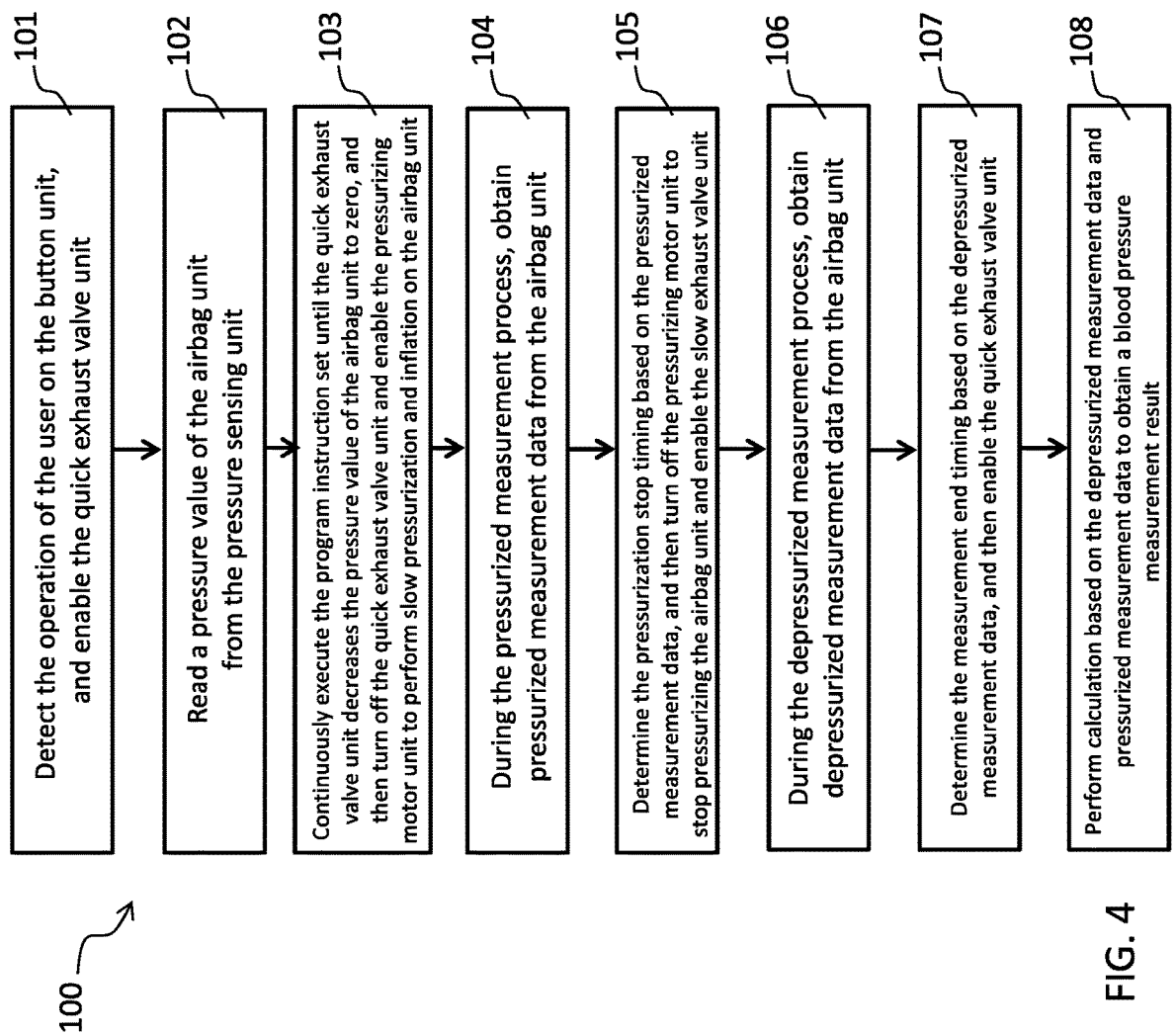
FIG. 4 is a flowchart of a blood pressure calculation method of the present invention.

In an embodiment of the present invention, a user can operate the button unit 13 to trigger the micro-processor unit 11 to execute the program instruction set stored in the memory 14; in an embodiment, the memory 14 can be embedded in the micro-processor unit 11, and the micro-processor unit 11 can execute the program instruction set to implement steps 101 to 108 of a blood pressure calculation method 100 shown in FIG. 4.

Please refer to FIG. 4, which shows a flowchart of a blood pressure calculation method of the present invention. The blood pressure calculation method 100 of the present invention includes steps 101 to 108. In a step 101, the micro-processor unit 11 executes the program instruction set to detect the operation of the user on the button unit 13, and then enable the quick exhaust valve unit 18 to quickly exhaust the airbag unit 19. In a step 102, the micro-processor unit 11 executes the program instruction set to read a pressure value of the airbag unit 19 from the pressure sensing unit 16. In a step 103, the micro-processor unit 11 continuously executes the program instruction set until the quick exhaust valve unit 18 decreases the pressure value of the airbag unit 19 to zero, and the micro-processor unit 11 then turns off the quick exhaust valve unit 18 and enables the pressurizing motor unit 15 to perform slow pressurization and inflation on the airbag unit 19.

Figure 5:
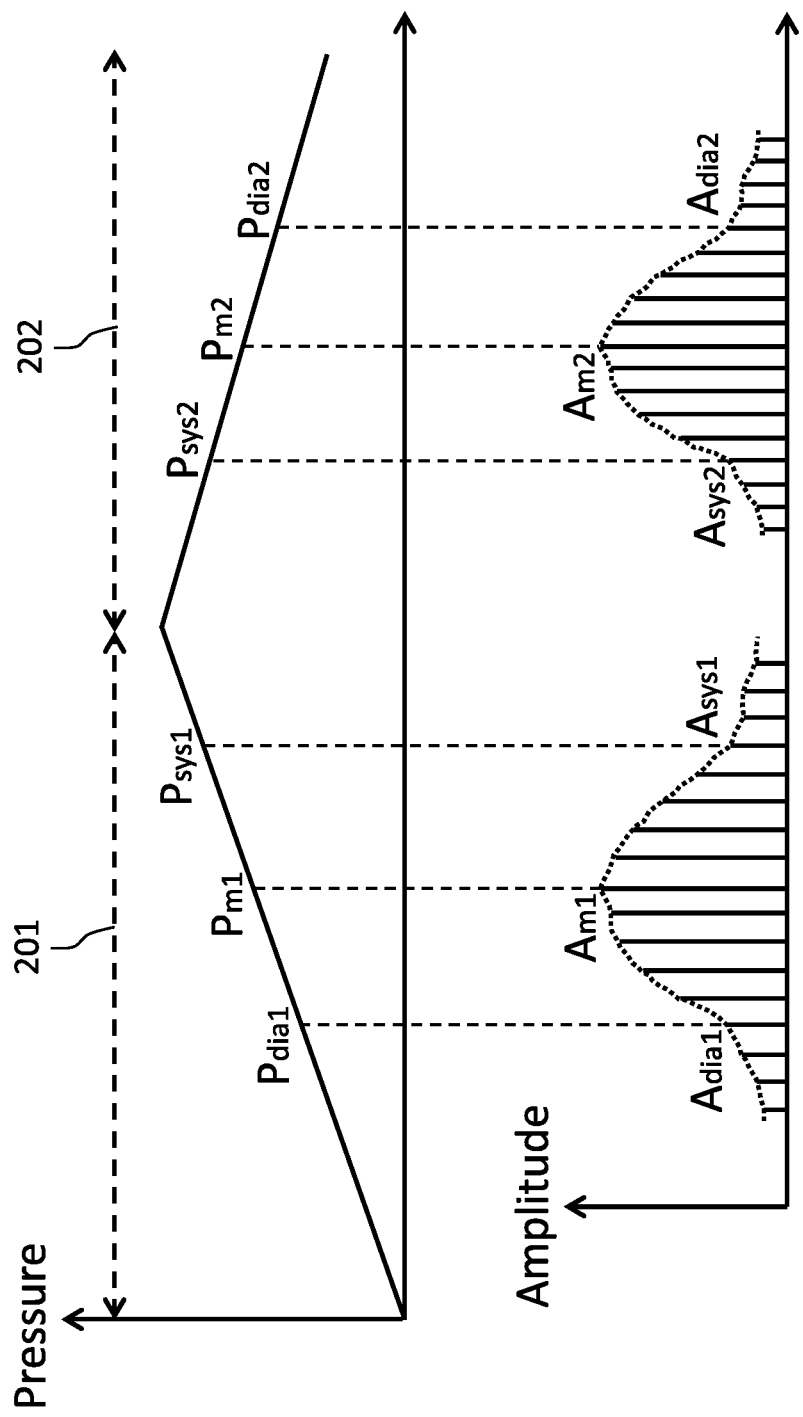
FIG. 5 is a schematic view of pulse signals and pressure values measured in single cycle of pressurization and depressurization of the blood pressure calculation method of the present invention.

Please refer to FIG. 5, which shows a schematic view of pulse signals and pressure values measured in single cycle of pressurization and depressurization of the blood pressure calculation method of the present invention. In a step 104, during the pressurized measurement process 201, the micro-processor unit 11 executes the program instruction set to obtain pressurized measurement data from the airbag unit 19 through the pressure sensing unit 16, and the pressurized measurement data can include amplitude data of a sequence of pulse signals, corresponding pressure data, and pulse interval data measured during the pressurized measurement process 201 shown in FIG. 5. In a step 105, the micro-processor unit 11 executes the program instruction set to determine the pressurization stop timing based on the pressurized measurement data, and then turn off the pressurizing motor unit 15 to stop pressurizing the airbag unit 19 and enable the slow exhaust valve unit 17 to slowly exhaust the airbag unit 19 according to the pressurization stop timing. In an embodiment, the pressurization stop timing can be the time when the amplitude of the extracted pulse is too small or no pulse signal can be extracted.

In a step 106, during the depressurized measurement process 202, the micro-processor unit 11 executes the program instruction set to obtain depressurized measurement data from the airbag unit 19 through the pressure sensing unit 16, and the depressurized measurement data can include the amplitude data of a sequence of pulse signals, the corresponding pressure data, and pulse interval data measured during the depressurized measurement process 202 shown in FIG. 5. In a step 107, the micro-processor unit 11 executes the program instruction set to determine the measurement end timing based on the depressurized measurement data, and then enable the quick exhaust valve unit 18 to quickly exhaust the airbag unit 19. In an embodiment, the measurement stop timing can be the time when the amplitude of the extracted pulse is too small or no pulse signal can be extracted. In a step 108, the calculation is performed based on the depressurized measurement data and pressurized measurement data to obtain a blood pressure measurement result, and a systolic pressure (Psys) and a diastolic pressure (Pdia) are displayed on the display output unit 12.

In the step 108 of the calculation method of the present invention, the micro-processor unit 11 can further execute the program instruction set to extract the at least one blood pressure parameter from each of the pressurized measurement data and the depressurized measurement data; in different embodiment of the present invention, the blood pressure parameter can include maximum amplitude data Am1 in pressurized measurement and maximum amplitude data Am2 in depressurized measurement, or a diastolic pressure value Pdia1 in pressurized measurement and a diastolic pressure value Pdia2 in depressurized measurement, or a systolic pressure value Psys1 in pressurized measurement and a systolic pressure value Psys2 in depressurized measurement. Next, the micro-processor unit 11 can further execute the program instruction set to perform calculation to obtain an average of the blood pressure parameters extracted from the pressurized measurement data and the depressurized measurement data; for example, the average can be, an average Am of the maximum amplitude data Am1 in pressurized measurement and the maximum amplitude data Am2 in depressurized measurement, as shown the following equation (5), to obtain a blood pressure measurement result.

In the step 108 of the blood pressure calculation method of the present invention, the micro-processor unit 11 can further execute the program instruction set to calculate a product of the average Am and a threshold parameter Tdia1 of the diastolic pressure in pressurized measurement and use the calculated product as an amplitude threshold Adia of the diastolic pressure in pressurized measurement, and the micro-processor unit 11 further executes the program instruction set to calculate a product of the average Am and a threshold parameter Tsys2 of the systolic pressure in depressurized measurement, and use the calculated product as an amplitude threshold Asys of the systolic pressure in depressurized measurement, and then extract or deduce pressure values from the pressurized measurement data and the depressurized measurement data based on the amplitude threshold Adia of the diastolic pressure in pressurized measurement and the amplitude threshold Asys of the systolic pressure in depressurized measurement, respectively, and use the pressure values as the diastolic pressure value Pdia and the systolic pressure value Psys of the blood pressure measurement result. The systolic pressure Psys and the diastolic pressure Pdia are displayed on the display output unit 12. In an embodiment, the threshold parameter Tdia1 of the diastolic pressure in pressurized measurement and the threshold parameter Tsys2 of the systolic pressure in depressurized measurement can be threshold values obtained from statistics of the clinical experimental results.

$$A_m = \frac{A_{m1} + A_{m2}}{2} \quad (5)$$

$$A_{dia} = A_m \times T_{dia1} \quad (6)$$

$$A_{sys} = A_m \times T_{sys2} \quad (7)$$

Figure 6:
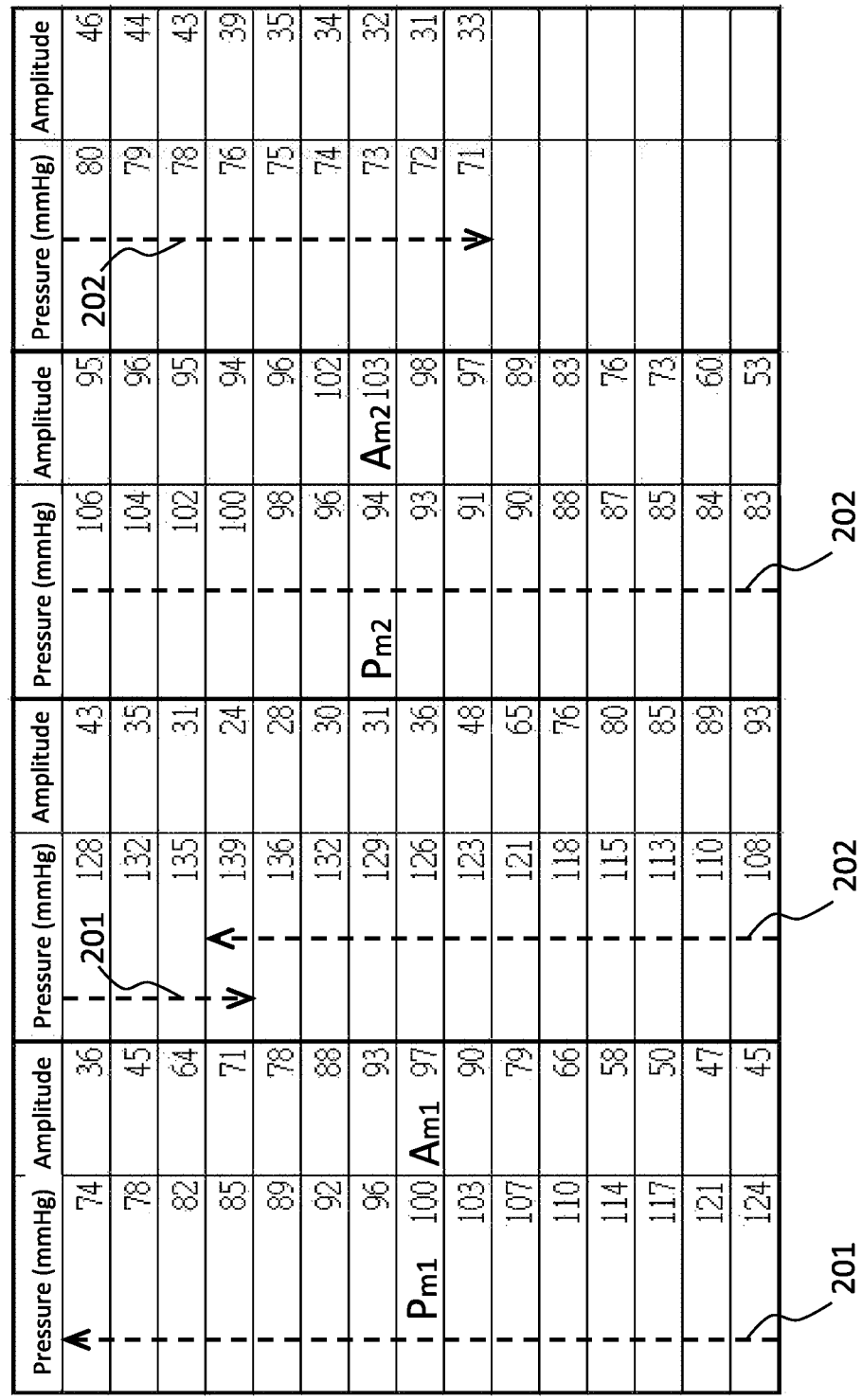
FIG. 6 is a measurement data table obtained in single cycle of pressurization and depressurization of the blood pressure calculation method of the present invention.

Please refer to FIG. 6, which shows a measurement data table obtained in single cycle of pressurization and depressurization of the blood pressure calculation method of the present invention. In an embodiment of the present invention, the blood pressure measurement device can perform single cycle of pressurization and depressurization of the blood pressure calculation method of the present invention to obtain amplitude data of a sequence of pulse signals and corresponding pressure data. The measurement data table shown in FIG. 6 includes the pressurized measurement data measured from the airbag unit 19 in pressurized measurement process 201, and the depressurized measurement data measured from the airbag unit 19 in depressurized measurement process 202.

In an embodiment of the present invention, according to statistics of clinical experimental results, the threshold parameter Tdia1 of the diastolic pressure in pressurized measurement is 0.45, and the threshold parameter Tsys2 of the systolic pressure in depressurized measurement is 0.8. In the step 108 of the blood pressure calculation method of the present invention, the maximum amplitude data Am1 (Am1=97) in pressurized measurement and the maximum amplitude data Am2 (Am2=103) in depressurized measurement are extracted from the sequence of the amplitude data of the pulse signals of the pressurized measurement data and the depressurized measurement data, respectively. The average Am of the maximum amplitude data Am1 in pressurized measurement and the maximum amplitude data Am2 in depressurized measurement is calculated to be 100. According to the equations (6) and (7), the amplitude threshold Adia of the diastolic pressure in pressurized measurement and the amplitude threshold Asys of the systolic pressure in depressurized measurement are calculated to be 45 and 80, respectively. Next, based on the amplitude threshold Adia (Adia=45) of the diastolic pressure in pressurized measurement, the search is performed in the sequence of the amplitude data of the pulse signal in the pressurized measurement data from the location where the maximum amplitude data Am1 in pressurized measurement is equal to 97, in the decreasing direction of the pressure value, such as the direction from Am1 to Adia1 shown in FIG. 5, to find the amplitude threshold Adia (Adia=45) of the diastolic pressure in pressurized measurement. After the amplitude threshold Adia with value of 45 is found, the pressure data, with value of 78, corresponding to amplitude threshold Adia, with value of 45, of the diastolic pressure in pressurized measurement can be extracted, and the pressure data with value of 78 is used as the diastolic pressure value Pdia, with value of 78, of the blood pressure measurement result.

Next, based on the amplitude threshold Asys, which is set as 80, of the systolic pressure in pressurized measurement, the search is performed in the sequence of the amplitude data of the pulse signal in the depressurized measurement data from the maximum amplitude data Am2 (Am2=103) in depressurized measurement in an increasing direction of the pressure value, such as the direction from Am2 to Asys2 shown in FIG. 5, to find the amplitude threshold Asys, with a value of 80, of the systolic pressure in depressurized measurement. After the amplitude threshold Asys with the value of 80 is found, the pressure data with a value of 115 and corresponding to amplitude threshold Asys (Asys=80) of the systolic pressure in depressurized measurement can be extracted and used as the systolic pressure value Psys, with the value of 115, of the blood pressure measurement result. Next, the systolic pressure value Psys with the value of 115 mmHg and the diastolic pressure value Pdia with the value of 78 mmHg are displayed on the display output unit 12.

Furthermore, during the process of searching the amplitude threshold Adia (Adia=45) of the diastolic pressure in pressurized measurement and the amplitude threshold Asys (Asys=80) of the systolic pressure in depressurized measurement from a sequence of the amplitude data of the pulse signal based on the calculation result, it is possible that there is no value directly corresponding to Adia or Asys in the sequence of measured amplitude data; therefore, in an embodiment of the present invention, two amplitude values approximate to each of Adia and Asys, and the corresponding pressure values can be found first, and the interpolation method can be performed on the two approximate amplitude values to deduce a pressure value corresponding to each of Adia and Asys based on a slope between the two approximate amplitude values, and the deduced pressure values can be used as the diastolic pressure value and the systolic pressure value of the blood pressure measurement result.

Figure 2:
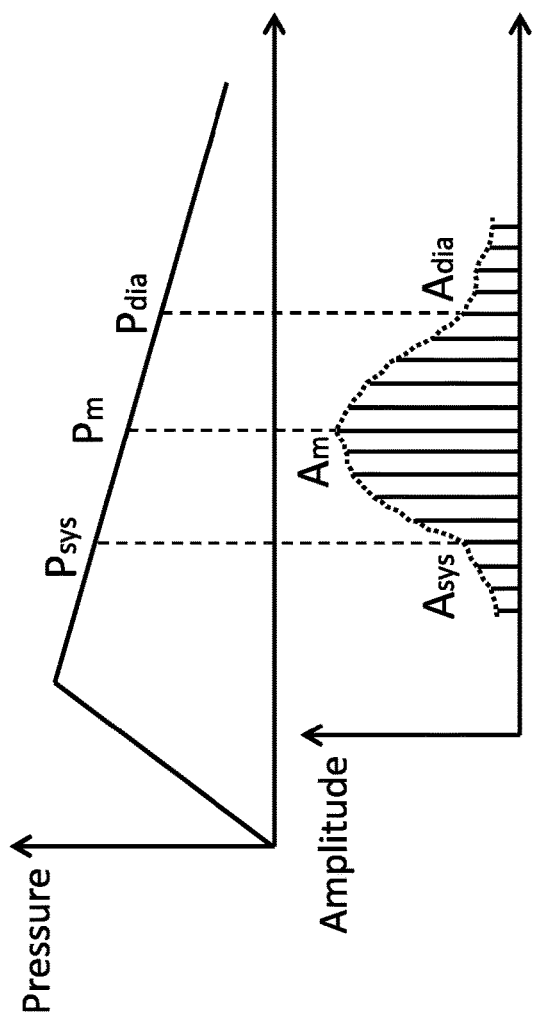
FIG. 2 is a schematic view of a pulse signal and pressure values measured by the conventional single-depressurization oscillography.

The present invention further provides an accuracy comparison between the blood pressure calculation method of the present invention and the conventional single-pressurization oscillography shown in FIG. 1 and the conventional single-depressurization oscillography shown in FIG. 2. The clinical test measures blood pressures of 30 people by using mercury auscultation as a standard manner, and each person measures 3 times, and a total of 90 pieces of comparison data are obtained. The pieces of data measure by the blood pressure calculation method of the present invention and by the conventional single-pressurization oscillography shown in FIG. 1 and the conventional single-depressurization oscillography shown in FIG. 2 are compared with the measurement results of the mercury blood pressure measurement device to score errors, the error within 5 mmHg is scored with 2, the error within 10 mmHg is scored with 1, the error exceeding 10 mmHg is scored with 0, and full score is 180 (100%). The statistics result is shown in the table below.

| Blood pressure measurement manner | Systolic pressure (Psys) | Diastolic pressure (Pdia) | Average score |
|---|---|---|---|
| Single-pressurization oscillography | 69% | 90% | 80% |
| Single-depressurization oscillography | 89% | 76% | 83% |
| The method of the present invention | 89% | 90% | 90% |

According to the comparison of the statistics results, the average score of the measured systolic pressure (Psys) and the diastolic pressure (Pdia) of the blood pressure calculation method of the present invention is higher than that of the conventional single-pressurization oscillography and the single-depressurization oscillography Furthermore, according to the statistics result, it is obvious that the blood pressure calculation method of the present invention can improve the accuracy of the obtained systolic pressure (Psys) and the diastolic pressure (Pdia) because of precluding the data of systolic pressure (Psys) obtained in pressurized measurement and collecting correct depressurized measurement data to obtain systolic pressure (Psys), and precluding the data of the diastolic pressure (Pdia) obtained in depressurized measurement and collecting correct pressurized measurement data to obtain diastolic pressure (Pdia).

In an embodiment of the present invention, the depressurized measurement data is used to obtain data of the systolic pressure (Psys) only, so in the step 107 of the blood pressure calculation method of the present invention, the measurement stop timing can be set as the time after the values of the maximum amplitude data Am2 in depressurized measurement and corresponding pressure are captured, and the quick exhaust valve unit 18 can then be enabled to complete the measurement. Furthermore, the micro-processor unit 11 can execute the program instruction set to further determine atrial fibrillation based on pulse interval data of the pressurized measurement data and the depressurized measurement data obtained in single pressurization process and depressurization process.

The atrial fibrillation determination method of the present invention includes flows (A) to (C) described below.

(A) Signal pre-processing (Per-Processing) flow including following steps. First, the blood pressure measurement device of the present invention captures the pulse signals of human body through the pressure sensor and the arm air bag; secondly, an analog-to-digital conversion device (ADC) is used to collect data signals at a fixed period; thirdly, a digital band-pass filter is used to filter out noise, which may be caused by hand muscle fibrillation or jitter, of the data signal and amplify the data signal; fourthly, peak features of the pulses are extracted by an mean and multi-point comparison and feature extraction method; fifthly, the pulse interval data is calculated based on a sampling rate and peak-to-peak sampling points.

(B) Feature extraction flow for extracting features of atrial fibrillation (AF) by using the following manners (i) to (iv):

(i) root mean square of the successive difference (RMSSD) and mean:

The coefficient of variation (CV) value is generally used to estimate the degree of data dispersion. The coefficient of variation of a set of data is defined as the percentage expression of the standard deviation (SD) of the set of data divided by the mean (M) of the set of data, and the standard deviation formula is expressed as follows:

$$SD = \sqrt{\frac{1}{N}\sum_{i=1}^{N}(x_i - M)^2} \quad (1)$$

$$M = \frac{\sum_{i=1}^{N} x_i}{N} \quad (2)$$

Where X is a sequence of data (such as interval of blood pressure pulse signals), N is the number of data samples, and M is the mean value of the data samples; as known from the above formula, when the number (N) of the sample data is more, the SD becomes more stable; in contrast, when the number (N) of sample data is less, the SD becomes more unstable; therefore, the standard deviation SD is more suitable as a statistical factor for long-term monitoring data. For short-term monitoring, RMSSD can be used for evaluation, and the formula is expressed as follows:

$$RMSSD = \sqrt{\frac{\sum_{i=1}^{N-1}(x_{i+1} - x_i)^2}{N-1}} \quad (3)$$

The ratio of RMSSD to mean (M) can be used to estimate the degree of short-term data dispersion.

(ii) Shannon entropy (ShEn):

Shannon entropy (ShEn) is a parameter statistic value used to measure the uncertainty of random variables. ShEn is related to the complexity of the data set and the ability of the data set to predict future data pointing from past data points. ShEn is one of the parameter tests in the AF calculation method of the present invention. Therefore, similar to RMSSD, ShEn is highly sensitive to abnormal value, and ShEn is between 0 and 1 (including 0 and 1) for any data set. A fully predictable single constant value has a ShEn value of zero. Completely random data (such as white noise) has ShEn close to 1. The present invention uses the generally acceptable assumption that atrial fibrillation is associated with higher uncertainty, so ShEn value of atrial fibrillation is higher than that of normal sinus rhythm. The formula is expressed as follows:

$$ShEn = \sum_{i=1}^{16} p(i) \frac{\log(p(i))}{\log\left(\frac{1}{16}\right)} \quad (4)$$

(iii) turning points ratio (TPR):

Turning point ratio (TPR) is a non-parametric statistic used to measure the randomness of fluctuations in a data set. It is the only non-parametric test used in the AF calculation method of the present invention, so unlike ShEn and RMSSD, TPR is not affected by hypothesis about the distribution of the data set. The turning point is a point with a value higher than that of the previous and next one, or lower than that of the previous and next one. TPR is calculated by comparing the number of turning points in the data set with the maximum number of possible turning points. The turning point ratio calculation assumes that the data is stationary, especially the fluctuation is random and not faster or less frequent than explained by chance alone; in this case, the data contains trends. The statistical test used in the algorithm uses the null hypothesis H0 in which the sequence is stationary, and the other hypothesis H1 in which the sequence is non-stationary. More specifically, the null hypothesis is that the pulse interval is random and therefore corresponds to AF; the alternative hypothesis is that the pulse interval is non-random and corresponds to normal sinus rhythm. Any random data, such as white noise, is expected to have a turning point about every 1.5 data points.

(iv) frequency-domain analysis:

The extracted pulse signal is converted into a frequency spectrum by Fourier transform, and then clutter can be obtained based on statistics of peak points of the spectrum.

(C) Estimation flow for determining whether atrial fibrillation exists according to collection of clinical data and the found best determination criteria.

The present invention disclosed herein has been described by means of specific embodiments. However, numerous modifications, variations and enhancements can be made thereto by those skilled in the art without departing from the spirit and scope of the disclosure set forth in the claims.

What is claimed is:

1. A blood pressure calculation method applied with a blood pressure measurement device comprising a pressurizing motor unit and at least one exhaust valve unit in communication with an airbag unit, the blood pressure calculation method comprising:

controlling the pressurizing motor unit to pressurize the airbag unit;

measuring pressurized measurement data from the airbag unit during a pressurization process;

controlling the pressurizing motor unit to stop pressurizing the airbag unit, and then controlling the at least one exhaust valve unit to depressurize the airbag unit;

measuring depressurized measurement data from the airbag unit during a depressurization process, wherein each of the pressurized measurement data and the depressurized measurement data comprises amplitude data of a sequence of pulse signals and pressure data corresponding to the amplitude data of the sequence of pulse signals;

extracting blood pressure parameters from each of the pressurized measurement data and the depressurized measurement data;

calculating an average of the blood pressure parameters extracted from the pressurized measurement data and the depressurized measurement data to obtain a blood pressure measurement result;

extracting maximum amplitude data from the pressurized measurement data and maximum amplitude data from the depressurized measurement data;

calculating an average of the maximum amplitude data extracted from the pressurized measurement data and the maximum amplitude data extracted from the depressurized measurement data;

calculating a product of the average of the maximum amplitude data extracted from the pressurized measurement data and the maximum amplitude data extracted from the depressurized measurement data and a threshold parameter of a systolic pressure in depressurized measurement, and using the product calculated as an amplitude threshold of the systolic pressure in depressurized measurement; and extracting or deducing pressure data from the depressurized measurement data based on the amplitude threshold of the systolic pressure in depressurized measurement, and using the pressure data as a systolic pressure value of the blood pressure measurement result.

2. A blood pressure calculation method applied with a blood pressure measurement device comprising a pressurizing motor unit and at least one exhaust valve unit in communication with an airbag unit, the blood pressure calculation method comprising:

controlling the pressurizing motor unit to pressurize the airbag unit;

measuring pressurized measurement data from the airbag unit during a pressurization process;

controlling the pressurizing motor unit to stop pressurizing the airbag unit, and then controlling the at least one exhaust valve unit to depressurize the airbag unit;

measuring depressurized measurement data from the airbag unit during a depressurization process, wherein each of the pressurized measurement data and the depressurized measurement data comprises amplitude data of a sequence of pulse signals and pressure data corresponding to the amplitude data of the sequence of pulse signals;

extracting blood pressure parameters from each of the pressurized measurement data and the depressurized measurement data;

calculating an average of the blood pressure parameters extracted from the pressurized measurement data and the depressurized measurement data to obtain a blood pressure measurement result;

extracting maximum amplitude data from the pressurized measurement data and maximum amplitude data from the depressurized measurement data;

calculating an average of the maximum amplitude data extracted from the pressurized measurement data and the maximum amplitude data extracted from the depressurized measurement data;

calculating a product of the average of the maximum amplitude data extracted from the pressurized measurement data and the maximum amplitude data extracted from the depressurized measurement data and a threshold parameter of a diastolic pressure in pressurized measurement, and using the product calculated as an amplitude threshold of the diastolic pressure in pressurized measurement; and extracting or deducing pressure data from the pressurized measurement data based on the amplitude threshold of the diastolic pressure in pressurized measurement, and using the pressure data as a diastolic pressure value of the blood pressure measurement result.

3. A blood pressure measurement device, comprising:

an airbag unit;

a pressurizing motor unit in communication with the airbag unit;

at least one exhaust valve unit in communication with the airbag unit;

a sensing unit configured to obtain measurement data from the airbag unit;

a display unit configured to display a blood pressure measurement result;

a memory configured to store a program instruction set; and a processing unit configured to execute the program instruction set to:

control the pressurizing motor unit to pressurize the airbag unit;

receive pressurized measurement data from the sensing unit during a pressurization process;

control the pressurizing motor unit to stop pressurizing the airbag unit, and then control the at least one exhaust valve unit to depressurize the airbag unit;

receive depressurized measurement data from the sensing unit during a depressurization process;

extract blood pressure parameters from each of the pressurized measurement data and the depressurized measurement data;

calculate an average of the blood pressure parameters extracted from the pressurized measurement data and the depressurized measurement data to obtain the blood pressure measurement result;

extract maximum amplitude data from the pressurized measurement data and maximum amplitude data from the depressurized measurement data; and calculate an average of the maximum amplitude data extracted from the pressurized measurement data and the maximum amplitude data extracted from the depressurized measurement data;

calculate a product of the average of the maximum amplitude data extracted from the pressurized measurement data and the maximum amplitude data extracted from the depressurized measurement data and a threshold parameter of a systolic pressure in depressurized measurement, and use the product calculated as an amplitude threshold of the systolic pressure in the depressurized measurement; and extract or deduce pressure data from the pressurized measurement data, based on the amplitude threshold of the systolic pressure in depressurized measurement, and use the pressure data as a systolic pressure value of the blood pressure measurement result.

4. A blood pressure measurement device, comprising:

an airbag unit;

a pressurizing motor unit in communication with the airbag unit;

at least one exhaust valve unit in communication with the airbag unit;

a sensing unit configured to obtain measurement data from the airbag unit;

a display unit configured to display a blood pressure measurement result;

a memory configured to store a program instruction set; and a processing unit configured to execute the program instruction set to:

control the pressurizing motor unit to pressurize the airbag unit;

receive pressurized measurement data from the sensing unit during a pressurization process;

control the pressurizing motor unit to stop pressurizing the airbag unit, and then control the at least one exhaust valve unit to depressurize the airbag unit;

receive depressurized measurement data from the sensing unit during a depressurization process;

extract blood pressure parameters from each of the pressurized measurement data and the depressurized measurement data;

calculate an average of the blood pressure parameters extracted from the pressurized measurement data and the depressurized measurement data to obtain the blood pressure measurement result;

extract maximum amplitude data from the pressurized measurement data and maximum amplitude data from the depressurized measurement data; and calculate an average of the maximum amplitude data extracted from the pressurized measurement data and the maximum amplitude data extracted from the depressurized measurement data;

calculate a product of the average of the maximum amplitude data extracted from the pressurized measurement data and the maximum amplitude data extracted from the depressurized measurement data and a threshold parameter of a diastolic pressure in pressurized measurement, and use the product calculated as an amplitude threshold of the diastolic pressure in the pressurized measurement; and extract or deduce pressure data from the depressurized measurement data, based on the amplitude threshold of the diastolic pressure in the pressurized measurement, and use the pressure data as a diastolic pressure value of the blood pressure measurement result.

* * * * *